United States Patent [19]

Hori et al.

[11] Patent Number: 5,132,122
[45] Date of Patent: Jul. 21, 1992

[54] PROCESS FOR PRODUCING A LACTIC ACID DRINK

[75] Inventors: Toshiaki Hori, Nakajomachi; Hitoshi Kume, Houya; Akemi Hiramatsu, Tachikawa; Iwao Sakauchi, Murayama; Sennosuke Tokumaru, Fujisawa, all of Japan

[73] Assignees: Kyodo Milk Industry Co., Ltd., Tokyo; Nihon Kefia Co., Ltd., Fujisawa, both of Japan

[21] Appl. No.: 563,125

[22] Filed: Aug. 6, 1990

[51] Int. Cl.$^5$ ............................................. A23C 9/123
[52] U.S. Cl. ........................................ 426/42; 426/41; 426/43; 426/61; 426/62; 426/583; 426/592
[58] Field of Search ............. 426/41, 42, 43, 61, 426/62, 583, 592

[56] References Cited

FOREIGN PATENT DOCUMENTS 1135540 6/1986 Japan .
3146748 6/1988 Japan .

Primary Examiner—Jeanette Hunter
Assistant Examiner—Helen Pratt
Attorney, Agent, or Firm—Armstrong & Kubovcik

[57] ABSTRACT

A transparent lactic acid bacteria drink, which is a fermentation product obtained by allowing kefir fungi to ferment a milk material under forced supply of an oxygen-containing gas, comprises a casein protein-free whey component as the major component together with 3 to 20% of nonfat milk solids and 0.1 to 1.5% of ethanol, is disclosed. This lactic acid bacteria drink can be produced by a process which comprises allowing kefir fungi to ferment a milk material under forced supply of an oxygen-containing gas, removing a precipitate including casein protein and then sterilizing the supernatant by filtering or pasteurizing the same by heating.

6 Claims, No Drawings

PROCESS FOR PRODUCING A LACTIC ACID DRINK

BACKGROUND OF THE INVENTION

This invention relates to a lactic acid bacteria drink and a process for the production of the same. More particularly, it relates to a lactic acid bacteria drink, which is a fermentation product produced by kefir fungi in the form of a transparent refreshing drink and exerts an immunoinvigoration effect, and a process for the production of the same.

Kefir is a traditional milk fermentation drink which originates from the Caucasus in Central Asia and has been popularized over a wide area including Europe. Kefir is produced by adding an appropriate amount of activated Kefir grains or a Kefir starter to a milk (mainly cow's milk or mare's milk) and then allowing the milk to undergo fermentation at 15° to 25° C. for one to two days.

The term "kefir fungi" as used herein means a natural symbion of various microorganisms which behave as a single organism from a biological viewpoint. The kefir fungi are generally provided as lyophilized or water-immersed kefir grains as large as an adzuki bean to the head of a little finger in the form of a white cauliflower. These kefir grains are inoculated usually into a milk medium and repeatedly cultured therein. The activated kefir grains thus obtained or the culture medium may be employed as a kefir starter.

The fermentation with the kefir fungi is mainly caused by lactic acid bacteria and yeasts originating from the kefir grains or the kefir starter. Namely, lactic acid fermentation is observed first, followed by yeast fermentation.

In the production of kefir, the full performance of the lactic acid fermentation and the yeast fermentation requires a prolonged fermentation time. In this case, furthermore, it is difficult to maintain well-balanced fermentation under the influence of other contaminating microorganisms. Thus this process is unsuitable for industrial production.

The yeast fermentation imparts a mellow flavor to the fermentation product which is never observed in common yoghurts. However the over fermentation, which occurs during the storage, causes the separation of whey, the excessive yeast odor and gassing, thus deteriorating the properties of the product.

On the other hand, it is difficult at present to sterilize or pasteurize the product so as to solve the above-mentioned problems caused by the over fermentation in order to stabilize the product.

This is because the fermentation product contains a large amount of casein protein, which makes it difficult to directly sterilize it by filtering. When the product is to be thermally pasteurized, a large amount of a sugar or a stabilizer should be added in order to prevent the agglutination of curd. These additives are liable to affect the viscosity or taste of the fermentation product, which might deteriorate the characteristic flavor of the kefir.

Japanese patent application Kokai publication No. 63-146748 proposed a process for the production of kefir free from these disadvantages. In this process, a whey component, to which a yeast flavor achieved by fermentation has been imparted, is pasteurized or sterilized and then mixed with a fermented milk. Thus a fermented milk product or a kefir-like product having a mellow flavor and a high stability can be obtained.

In the case of kefir, however, this process suffers from such problems that the yeast flavor is weakened or an increase in the solid milk content lowers the refreshness.

Meanwhile as regards the physiological activities of kefir, there have been reported an immunoinvigoration effect and an antithrombotic effect caused by polysaccharides. It is reported that the kefir fermentation product would exert similar effects.

However the extends and intensities of these effects vary from report to report. It is generally believed that the oral intake of kefir would bring about only limited effects and unstable reproduction.

SUMMARY OF THE INVENTION

A first object of the present invention resides in providing a lactic acid bacteria drink which is a fermentation product produced by kefir fungi in the form of a transparent refreshing drink and exerts an immunoinvigoration effect.

A second object of the present invention resides in providing a lactic acid bacteria drink which has a long shelf life, a mellow flavor and a refreshness.

A third object of the present invention resides in providing a process for the production of a lactic acid bacteria drink suitable for industrial production wherein both of lactic acid fermentation and yeast fermentation can be fully effected within a short period of time.

The first and second objects of the present invention can be achieved by a lactic acid bacteria drink which is a product obtained by allowing kefir fungi to ferment a milk material under forced supply of an oxygen-containing gas and contains a casein-free whey component as the major component together with 3 to 20% of nonfat milk solids and 0.1 to 1.5% of ethanol.

On the other hand, the third object of the present invention can be achieved by a process for the production of a lactic acid bacteria drink which comprises allowing kefir fungi to ferment a milk material under forced supply of an oxygen-containing gas, removing a precipitate including casein protein and sterilizing the supernatant by filtering or thermally pasteurizing the same.

PREFERRED EMBODIMENTS OF THE INVENTION

Now a process for the production of the lactic acid bacteria drink of the present invention will be described.

First, a kefir starter is prepared.

Either a starter prepared from commercially available kefir grains or a ready-made kefir starter may be employed in the present invention.

A starter is prepared from kefir grains in the following manner.

First, kefir grains are inoculated into a pasteurized milk medium (for example, cow's milk or defatted milk) at a concentration of 5 to 10%. Then they are incubated in the medium at 15° to 25° C. until the milk completely agglutinates.

Next, the medium is filtered through, for example, a net. The kefir grains thus collected are inoculated into a fresh medium at the same concentration and incubated therein at 15 to 25° C. until the milk completely agglutinates.

When this transplantation procedure is repeated, a milk medium completely agglutinates within 20 to 30 hours after the inoculation of kefir grains.

Thus activated kefir grains are obtained. Either these kefir grains per se or the culture medium thereof may be used as a kefir starter.

The residual kefir grains are available in the subsequent preparation of the additional starter.

Although a commercially available kefir starter may be used in accordance with the manufacturer's suggestion, it is preferable to activate it in a milk medium.

Next, the activated kefir grains or the kefir starter is applied to the fermentation of a milk material.

Examples of the milk material suitable for the present invention include cow's milk, defatted milk, reconstructed milk, whey and permeated cheese whey. The solid milk content of the milk material is to be adjusted to 3 to 20%.

Then the milk material is pasteurized.

The pasteurization is conducted either by heating to 80° to 95° C. for 10 to 20 minutes or by the UHT method or the HTST method. In order to prevent contamination during the fermentation, it is preferable to select a rather powerful pasteurization.

The pasteurized milk material is then inoculated with the above-mentioned activated kefir grains or the kefir starter at a ratio of 3 to 5%. Then fermentation is effected under forced aeration at 15° to 30° C. for approximately 10 to 20 hours.

The forced aeration may be conducted by supplying an oxygen-containing gas, which has been sterilized by passing through a filter, with the use of a common stirring agitator provided in a fermentation tank or by aeration.

Examples of the oxygen-containing gas include air, pure oxygen, a gaseous mixture of pure oxygen and nitrogen and a gaseous mixture of pure oxygen and air.

When an agitator is to be used, the fermented liquor is stirred to such an extent that a vortex is observed at the center of the surface of the fermented liquor (at 100 to 200 rpm). When aeration is to be conducted, about a fifth to equal volume relative to the fermentation liquid of the oxygen-containing gas may be blown into the bottom of the fermentation tank.

The degree of the fermentation may be monitored by the pH value and acidity (in the case of the lactic acid fermentation) or by the ethanol concentration (in the case of the yeast fermentation). When the desired level is achieved, the fermentation is ceased.

These levels vary depending on the employed starter. Generally speaking, the fermentation is to be ceased when a pH value of 3.8 to 5.0, an acidity of 0.39 to 0.9 or an ethanol concentration of 0.1 to 1.5% is achieved.

After the completion of the fermentation, the mixture is clarified followed by pasteurization or sterilization. These procedures vary depending on the employed materials. When a material containing a large amount of casein protein, such as cow's milk or defatted milk, is employed, it is first required to remove the curd formed by said protein.

The curd may be removed on an industrial scale through continuous centrifugation at 8,000 to 10,000 rpm. In this case, it is unavoidable that some curd remains in the product. In order to minimize the contamination with the curd, the curd may be preliminarily agglutinated by heating to 80° to 90° C.

After the removal of the casein protein (curd), the supernatant (i.e., whey) may be treated in the same manner as that employed for a fermented liquor mainly comprising whey obtained from whey or permeated cheese whey.

Namely, the supernatant should be clarified by ultrafiltration or ordinary filtration to thereby remove the residual curd or casein protein originating from the starter.

In the case of the ultrafiltration, membrane of a permeation molecular weight of 10,000 to 100,000 is employed and the permeating fraction is recovered. In the case of the ordinary filtration, a filter of a permeation pore of from 10 to 20 μm is employed. Further, a prefilter or a filtering aid may be employed to thereby improve the filtering performance.

The obtained filtrate is sterilized by using a filter or thermally pasteurized to thereby prolong the shelf life.

The sterilization may be conducted by using a filter of a pore size of 0.20 to 0.45 μm. The pasteurization may be conducted by heating to 80° to 90° C. for 10 to 15 minutes.

The fermented liquor thus obtained is filled in a sterile container (in the case of sterilization) or packed under the heat condition (in the case of pasteurization).

The lactic acid bacteria drink of the present invention thus obtained comprises a casein-free whey component as the major component together with 3 to 20% of nonfat milk solids and 0.1 to 1.5% of ethanol.

The lactic acid bacteria drink of the present invention, which is produced by conducting both of the lactic acid fermentation and yeast fermentation to the full extent within a short period of time and sterilizing by filtering or pasteurizing by heating without deteriorating the characteristic flavor of kefir, has a long shelf life, a mellow flavor and a refreshness.

Furthermore, the lactic acid bacteria drink of the present invention is a transparent refreshing drink, different from any known fermentation product of kefir fungi.

In addition, the lactic acid bacteria drink of the present invention exerts an intense immunoinvigoration effect.

To further illustrate the present invention, the following Examples will be given, wherein an acidity, an ethanol content and an immunoinvigoration effect were determined in the following manners.

Acidity: expressed by the acidity of lactic acid determined by titration.

Ethanol content: determined by an enzymatic method with the use of an ethanol determination kit produced by Boehringer Mannheim GmbH, West Germany.

Immunoinvigoration effect: mice aged seven weeks were divided into four groups each consisting of ten animals. To three test groups among the four, 10, 50 and 100 mg/day of a lyophilized sample were gastrically administered, while 100 mg/day of defatted milk powder was given to the control group.

On the seventh day of the administration, a 5% solution of picryl chloride in ethanol was applied to the abdominal part of each animal and the administration was continued. On the 14th day, a 1% solution of picryl chloride in olive oil was applied to the whole ears of each animal. 24 hours thereafter, the fibrous thickening of the ears caused by delayed hypersensitivity was evaluated. The evaluation was conducted by determining the difference in the thickness of the ears before and after the application and the degree of the thickening was expressed in percentage by supposing the value of the control group as 100. The obtained value was employed as an indication for the enhancement of immunoinvigoration.

EXAMPLE 1 AND COMPARATIVE EXAMPLE 1

Cow's milk was subjected to ultrafiltration with the use of a filter of a permeation molecular weight of 100,000. The filtrate was pasteurized at 80° C. for ten minutes and then cooled to 30° C. to thereby give a material to be fermented.

Separately, kefir grains (mfd. by Christian Hansen Laboratory, Denmark) were activated by subculturing in a cow's milk medium at a rate of 10%. 5% (based on the milk material) of the culture medium, which was employed as a kefir starter, was added to the milk material and fermentation was effected at 30° C. for ten hours while blowing 50% by volume (based on the starting material) of sterile air from the bottom of the fermentation tank.

The fermented liquor was then clarified by passing through a filter of a permeation molecular weight of 100,000 and then filled in a 100-ml transparent bottle under the heat condition. Thus the lactic acid bacteria drink of the present invention was obtained (Example 1).

Separately, cow's milk was pasteurized at 80° C. for ten minutes and cooled to 25° C. to thereby give a material to be fermented.

The same kefir starter as the one described above was inoculated into the above milk material at a rate of 5% and filled in a 100-ml transparent bottle under a sterile condition. Next, it was fermented at 5° C. for 20 hours to thereby give a comparative product (Comparative Example 1).

Table 1 shows the properties of the product of the present invention (Example 1) and those of the comparative product (Comparative Example 1).

As Table 1 clearly shows, the product of the present invention is superior to the comparative one in the yeast flavor and ethanol productivity, though the former product was produced through the fermentation within a shorter period of time. Furthermore, the product of the present invention showed an extremely prolonged shelf life and an improved immunoinvigoration effect.

TABLE 1

| Test item | Invention product | Comparative product |
| --- | --- | --- |
| Fermentation time | 10 hr | 20 hr |
| Acidity (%) | 0.51 | 0.78 |
| Ethanol (%) | 0.42 | 0.03 |
| Flavor | mellow yeast flavor | less yeast flavor |
| Appearance | transparent, yellowish green | white |
| Refreshness | remarkable | slight |
| Shelf life | no change in appearance or flavor after the storage at 5° C. for 6 months | whey separation, excessive yeast odor and gassing after the storage at 5° C. for 1 week |
| Immunoinvigoration** | 178% (50 mg)* | 143% (100 mg)* |

Note
*Figures in the parentheses indicate amounts of administration.
**the average of the group showing the maximum effect.

EXAMPLE 2

100 kg of cow's milk was subjected to ultrafiltration with the use of a filter of a permeation molecular weight of 10,000. 80 kg of the filtered milk thus obtained was pasteurized at 80° C. for ten minutes and then cooled to 30° C. to thereby give a material to be fermented.

Separately, 250 g of kefir grains (mfd. by Christian Hansen Laboratory, Denmark) were inoculated into 5 kg of a cow's milk medium and subcultured thrice at intervals of 24 hours to thereby activate the same. Next, 4 kg of the culture medium was added to 80 kg of the above-mentioned filtered milk and fermentation was effected at 30° C. for 12 hours while blowing 30 l/min of sterile air from the bottom of the fermentation tank.

The fermented liquor was then clarified by passing through a filter of a permeation molecular weight of 100,000, pasteurized at 80° C. and filled in 100-ml transparent bottles under the heat condition. Thus a lactic acid bacteria drink, which contained 5.65% of nonfat milk solids and 0.38% of ethanol and showed an acidity of 0.51, was obtained.

The obtained product was a kefir product having a mellow flavor, a refreshness and a transparent appearance with a vivid color. After the storage at 5° C. for three months, the product did not suffer from any change.

EXAMPLE 3

200 kg of cow's milk was pasteurized at 80° C. for ten minutes and then cooled to 25° C. 10 kg of a kefir culture (mfd. by Miles Co.) was added thereto and fermentation was effected in a 200-t fermentation tank at 25° C. for 18 hours while agitating at 80 rpm.

The fermented liquor was then centrifuged at 10,000 rpm to thereby give 153 kg of a whey. This whey was then clarified with a filter of a permeation molecular weight of 100,000 and pasteurized at 80° C. Then it was filled in 100-ml transparent bottles under the heat condition. Thus a clarified lactic acid bacteria drink, which comprised 5.70% of nonfat milk solids and 0.33% of ethanol and showed an acidity of 0.62, was obtained.

The obtained product was similar to the one obtained in Example 1 and showed a high stability.

As described above, the lactic acid bacteria drink of the present invention, which can be sterilized by filtering or pasteurized by heating without deteriorating the characteristic kefir flavor, has a long shelf life, a mellow flavor, a refreshness and a transparent appearance with a vivid color. Further it exerts an intense immunoinvigoration effect. Thus it is expected as a highly useful health drink.

Further, the process for the production of a lactic acid bacteria drink of the present invention, wherein the forced supply of an oxygen-containing gas makes it possible to conduct both of lactic acid fermentation and yeast fermentation to the full within a short period of time, is suitable for the production of a lactic acid bacteria drink on an industrial scale.

What is claimed is:

1. A process for the production of a lactic acid bacteria drink, which comprises: fermenting a milk material with kefir fungi at a temperature of 15° to 30° C. for 10 to 20 hours while one-fifth to an equal amount of oxygen-containing gas, based on the volume of the milk material, is blown into the milk material per minute to thereby permit a yeast fermentation and a lactic acid bacteria fermentation to take place at the same time; terminating the fermentation as soon as the fermentation mixture attains a pH of 3.8 to 5.0, an acidity of 0.39 to 0.9 and an ethanol concentration of 0.1 to 1.5%, removing precipitated casein; and thereafter subjecting the resulting fermentation product to a sterilization by filtering or a pasteurization by heating.

2. A process as claimed in claim 1, wherein said kefir fungi are activated kefir grains or a kefir starter.

3. A process as claimed in claim 1, wherein said milk material is selected from the group consisting of cow's milk, defatted milk, reconstructed milk, whey and permeated cheese whey.

4. A process as claimed in claim 1, wherein said oxygen-containing gas is selected from the group consisting of air, pure oxygen, a gaseous mixture of pure oxygen and nitrogen and a gaseous mixture of pure oxygen and air.

5. A process as claimed in claim 1, wherein said sterilization by filtering is conducted with the use of a filter of a pore size of 0.20 to 0.45 $\mu$m.

6. A process as claimed in claim 1, wherein said pasteurization by heating is conducted by heating the fermented liquor to 80° to 90° C. for 10 to 15 minutes.

* * * * *